United States Patent
Voic et al.

(10) Patent No.: US 10,835,276 B2
(45) Date of Patent: Nov. 17, 2020

(54) ULTRASONIC SURGICAL SYSTEM FOR OSSEOUS TRANSECTION

(71) Applicant: MISONIX, INCORPORATED, Farmingdale, NY (US)

(72) Inventors: Dan Voic, Cedar Grove, NJ (US); Paul Mikus, Trabuco, CA (US)

(73) Assignee: MISONIX, INCORPORATED, Farmingdale, NY (US)

(*) Notice: Subject to any disclaimer, the term of this patent is extended or adjusted under 35 U.S.C. 154(b) by 88 days.

(21) Appl. No.: 16/243,816

(22) Filed: Jan. 9, 2019

(65) Prior Publication Data
US 2019/0209199 A1 Jul. 11, 2019

Related U.S. Application Data

(60) Provisional application No. 62/616,192, filed on Jan. 11, 2018.

(51) Int. Cl.
| | | |
|---|---|---|
| *A61B 17/32* | (2006.01) | |
| *A61B 17/16* | (2006.01) | |
| *A61B 34/30* | (2016.01) | |
| *A61B 90/50* | (2016.01) | |
| A61B 17/00 | (2006.01) | |
| A61B 90/00 | (2016.01) | |

(52) U.S. Cl.
CPC .. *A61B 17/320068* (2013.01); *A61B 17/1626* (2013.01); *A61B 17/1628* (2013.01); *A61B 34/30* (2016.02); *A61B 90/50* (2016.02); *A61B 2017/00026* (2013.01); *A61B 2017/00141* (2013.01); *A61B 2017/320075* (2017.08); *A61B 2090/064* (2016.02)

(58) Field of Classification Search
CPC .................. A61B 17/320068; A61B 34/30
See application file for complete search history.

(56) References Cited

U.S. PATENT DOCUMENTS

| | | | | |
|---|---|---|---|---|
| 6,666,860 | B1* | 12/2003 | Takahashi | A61B 17/320068 606/34 |
| 2003/0208296 | A1* | 11/2003 | Brisson | B33Y 50/02 700/117 |
| 2007/0083209 | A1* | 4/2007 | Schenberger | A61B 17/142 606/82 |
| 2007/0287934 | A1* | 12/2007 | Babaev | A61B 17/320068 601/2 |

(Continued)

FOREIGN PATENT DOCUMENTS

| | | |
|---|---|---|
| EP | 0732082 A2 | 9/1996 |
| EP | 1504399 A2 | 2/2005 |

*Primary Examiner* — Christian A Sevilla
(74) *Attorney, Agent, or Firm* — R. Neil Sudol; Henry D. Coleman

(57) ABSTRACT

A surgical system for transecting osseous tissue includes an ultrasonic waveform generator, a control unit, an ultrasonic instrument assembly including a electromechanical transducer and an ultrasonic blade, and a robotic system. The ultrasonic instrument assembly is attached to the robotic arm. The surgical system is configured so that the robotic arm moves the ultrasonic blade at a constant forward feed speed through the bone during a cutting operation and so that the forward motion is reduced, and preferably halted automatically upon a reduction in load per unit time or applied power, as monitored by a pickup or sensor.

13 Claims, 1 Drawing Sheet

(56) References Cited

U.S. PATENT DOCUMENTS

| | | | | |
|---|---|---|---|---|
| 2008/0194999 A1* | 8/2008 | Yamaha | ......... | A61B 17/320068 601/2 |
| 2010/0125292 A1* | 5/2010 | Wiener | .......... | A61B 17/320068 606/169 |
| 2014/0188111 A1* | 7/2014 | Weber | .................. | A61B 18/148 606/49 |

* cited by examiner

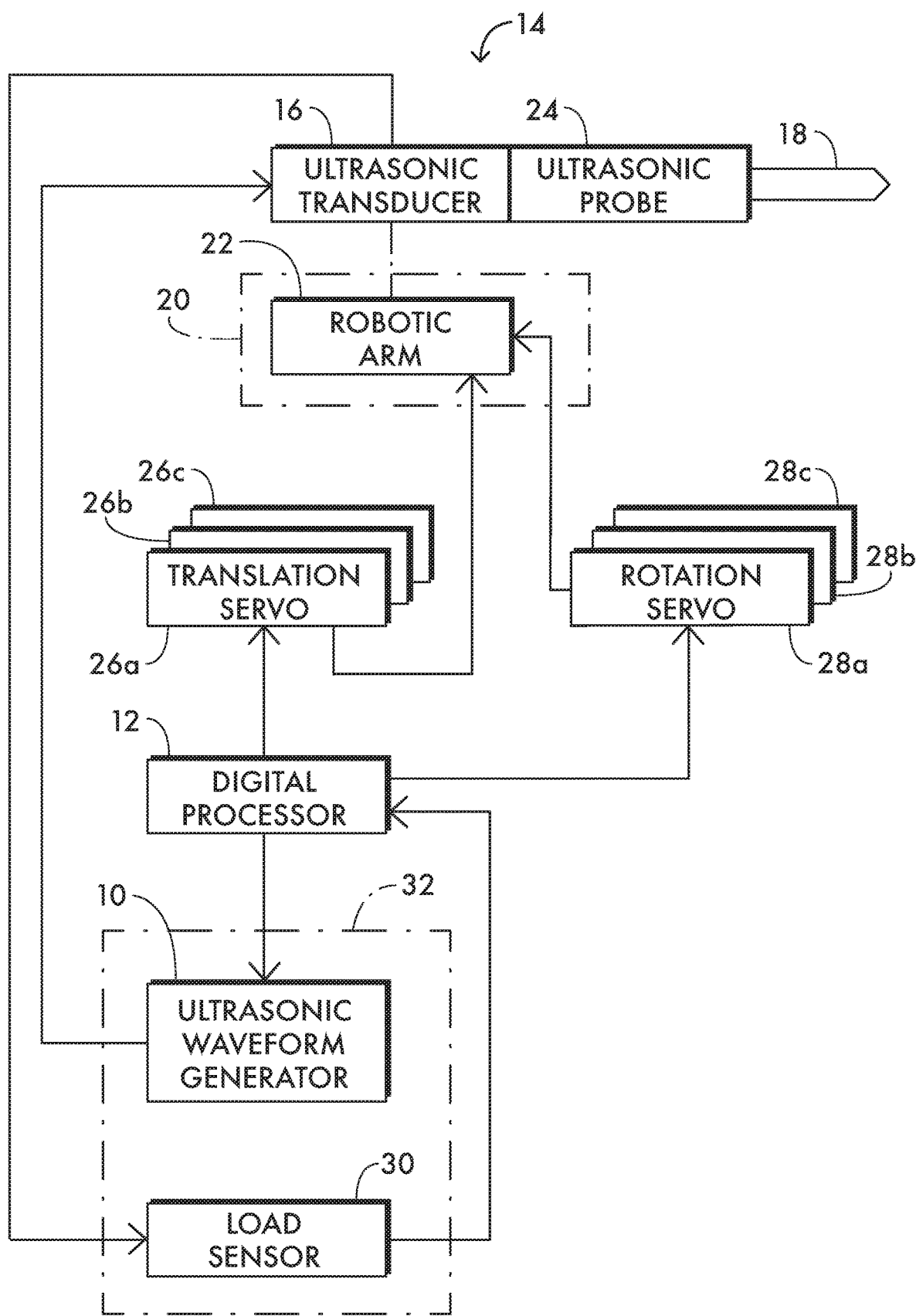

ULTRASONIC SURGICAL SYSTEM FOR OSSEOUS TRANSECTION

BACKGROUND OF THE INVENTION

This invention relates to an ultrasonic surgical system particularly useful in the transecting of spinal bone tissue. This invention also relates to an associated surgical method.

Over the past 30 years, several ultrasonic tools have been invented which can be used to ablate or cut tissue in surgery. Wuchinich et al. in U.S. Pat. No. 4,223,676 and Idemoto et al in U.S. Pat. No. 5,188,102 disclose such devices.

Ultrasonic surgical devices generally fall into two categories. One is a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as microstreaming of bubbles in the tissue matrix. The effect is that the tissue becomes liquefied and separated. It then becomes emulsified with the irrigant solution. The resulting emulsion is then aspirated from the site. Bulk excision of tissue is possible by applying the energy around and under unwanted tumors to separate it from the surrounding structure. The surgeon can then lift the tissue out using common tools such as forceps.

A second kind of ultrasonic device uses a sharp blade instead of a blunt hollow probe. Here a cutting action takes place. Such a sharp ultrasonic blade is the subject of U.S. Pat. No. 6,379,371. As disclosed therein, the blade shape is semicircular at the distal portion with two straight sides parallel to the longitudinal axis and extending back to the shoulder that contacts the vibrating probe. Male threads are shown which mate with the female threaded socket of the probe (or transducer) to allow tight intimate contact of the probe and blade tip shoulder. When the two are torqued together, they form a single resonant body that will vibrate in sympathy with the transducer and generator combination. The distal end of the blade will vibrate with an amplitude set by the mechanical gain of the probe/tip geometry and the input amplitude provided by the transducer generator combination. This motion provides the cutting action for the tissue in question.

The blade of U.S. Pat. No. 6,379,371 was intended for the cutting or excising of bone or similarly hard tissue in surgical applications. The blade is more effective in cutting hard tissue. Soft tissue will bounce off the blade. Soft tissue trapped between the blade and a hard surface, i.e. spinal cord can be harmed. In delicate operations, such as sinus lift surgery or craniotomies where the goal is to cut an aperture in the front of the skull to expose sinus tissue or brain but not cut the membrane directly beneath the bony structure, this difference on hard and soft issue is very important. It is also important in spinal and brain surgery where bone tissue must be cut with a minimum of damage to underlying soft tissues such as the dura mater. It was noted in early in vitro testing that the blade, if it plunged rapidly through the cortex of the bone, could puncture the membrane or rip it. After some experience, competent surgeons were able to master the technique, but the learning curve was steep.

U.S. patent application Ser. No. 14/211,586, filed Mar. 14, 2014, discloses a surgical method utilizing an ultrasonic surgical instrument with a blade having a thickness along a cutting edge of between about 0.0005 inch and about 0.020 inch. The method includes manually inserting the blade into bone tissue of a patient and ultrasonically vibrating the blade during the insertion procedure. Owing to the exigencies of the procedure, the blade prevents a surgeon from seeing at least a distal-most portion of the cutting edge during the inserting of the blade, as the distal-most portion of the cutting edge is located inside the patient. The surgeon manually terminates the inserting of the blade upon detecting via tactile sensation a change in resistance to advance of the blade indicating contact with soft tissue. While this technique is easier to master, there is still a need for an improved surgical methodology with ensured safety and efficacy. This is especially the case in spinal surgery where it is extremely important to avoid causing trauma to the spinal cord inside the spinal column.

OBJECTS OF THE INVENTION

An object of the present invention is to provide a surgical system for transecting osseous tissue in close proximity to vitally important structures, such as the spine.

A more specific object of the present invention is to provide such a surgical system that selectively transects osseous tissue while minimizing, and preferably eliminating, the risk of trauma to sensitive soft tissue nearby.

These and other objects of the invention will be apparent to those skilled in the art from the drawings and descriptions hereof. Although each object is attained by at least one embodiment of the invention, no embodiment need necessarily meet every object.

SUMMARY OF THE INVENTION

The present invention is directed to a surgical system for transecting osseous tissue in the close proximity of vitally important structures such as the spine. The system has, as principal components or subsystems, an ultrasonic waveform generator, a control unit, an ultrasonic instrument assembly including a electromechanical transducer and an ultrasonic blade, and a robotic system. The ultrasonic instrument assembly is attached to the robotic arm. In order to ensure safe operation, there should be no sudden surges in the instrument's penetration speed at the breakthrough point, that is at the point when the blade just penetrates through a distal side of a bone being cut. Pursuant to the invention, the surgical system is configured so that the robotic arm moves the ultrasonic blade at a constant forward feed speed through the bone during a cutting operation, the forward motion being reduced, and preferably halted automatically upon a reduction in load per unit time or applied power, as monitored by a pickup or sensor. Alternatively or additionally, power applied to the transducer via the waveform generator may be curtailed or interrupted.

The constant feed speed is maintained by servo controls of the robotic arm. The load change pickup is based on a feedback loop of the ultrasonic power application components (control unit, waveform generator, transducer), more precisely the variation of the drive voltage as a function of load. In order to maintain a constant motional amplitude, the ultrasonic controls maintain a constant motional current and phase angle while alternatively increasing and decreasing the ultrasonic voltage as a function of rising and falling load. At the breakthrough point, a voltage drop, associated with a decreased load, will be used as input to the servo controls for stopping the servo-driven motion. Additionally, the power output of the ultrasonic waveform generator may be at least substantially reduced or interrupted.

A surgical system comprises, in accordance with the present invention, a bone cutting blade, an ultrasonic electromechanical transducer, a robotic arm, a control processor, and an electrical waveform generator. The bone cutting blade has a cutting edge and is configured for transmitting ultrasonic vibrational energy, operatively connected to the ultrasonic electromechanical transducer, and mounted to the robotic arm. The control processor is operatively connected to the robotic arm and configured in part for controlling motion of the robotic arm so that the robotic arm moves the bone cutting blade at a constant or uniform rate through bone tissue during a cutting operation. The electrical waveform generator is operatively connected to the ultrasonic electromechanical transducer for energizing same to energize the bone cutting blade with ultrasonic mechanical waveform energy. The processor is operatively connected to the electrical waveform generator and configured therewith to monitor load on ultrasonic electromechanical transducer. The processor is further configured to undertake, upon sensing a reduction in load or applied power, a control action taken from the group consisting of inducing the robotic arm to halt motion of the bone cutting blade and at least substantially reducing waveform energy output of the waveform generator.

An associated surgical method comprises providing an ultrasonic bone cutting blade operatively connected to an ultrasonic electromechanical transducer; mounting the ultrasonic bone cutting blade and the ultrasonic electromechanical transducer to a robotic arm, and via a plurality of servomechanisms actuating the robotic arm to move the ultrasonic bone cutting blade at a constant or uniform rate through bone tissue during a surgical cutting operation. The method also comprises operating an electrical waveform generator to energize the ultrasonic electromechanical transducer to vibrate the ultrasonic bone cutting blade at an ultrasonic frequency during the surgical cutting operation. The operating of the electrical waveform generator includes adjusting power output thereof to maintain a constant vibrational amplitude of the ultrasonic bone cutting blade. Furthermore, the method includes automatically monitoring load or power output of the electrical waveform generator and, upon sensing a reduction in load or applied power, operating the servomechanisms to actuate the robotic arm to halt motion of the ultrasonic bone cutting blade and optionally at least substantially reducing waveform energy output of the waveform generator.

A surgical system for transecting osseous tissue in close proximity to vitally important structures comprises, in accordance with the present invention, an ultrasonic waveform generator, a control unit operatively connected to the ultrasonic waveform generator, and an ultrasonic instrument assembly including an electromechanical transducer and an ultrasonic blade. The ultrasonic waveform generator is operatively connected to the transducer for energizing same. The system further comprises a robotic subsystem including servomechanisms and a robotic arm movable by the servomechanisms. A load sensor or pickup component is operatively connected to the electromechanical transducer and included in the ultrasonic waveform generator, the load sensor or pickup component being operatively connected to the control unit. The ultrasonic instrument assembly is attached to the robotic arm, while the control unit is operatively connected to the servomechanisms and configured to actuate the robotic arm so as to move the ultrasonic blade at a constant forward feed rate through bone tissue during a cutting operation. The control unit is additionally configured to operate the servomechanisms, in response to a drop in load per unit time or applied power as detected by the load sensor or pickup component, to at least reduce forward motion of the ultrasonic blade through the bone tissue automatically. Optionally, the control unit is further configured to at least substantially reduce power output of the ultrasonic signal generator automatically in response to a drop in load per unit time or applied power as detected by the load sensor or pickup component.

A related surgical method for transecting osseous tissue in close proximity to vitally important structures comprises operating an ultrasonic waveform generator to output an ultrasonic waveform signal of a preselected frequency, feeding the ultrasonic waveform signal to an electromechanical transducer of an ultrasonic instrument assembly including an ultrasonic blade, generating an ultrasonic standing wave in the ultrasonic instrument assembly including the ultrasonic blade, and controlling a robotic subsystem including servomechanisms and a robotic arm movable by the servomechanisms, to move the ultrasonic blade at a constant forward feed rate through bone tissue during a cutting operation, where the ultrasonic instrument assembly is mounted to the robotic arm. In response to a drop in load or applied power as detected via a load sensor or pickup component, the robotic subsystem is controlled to terminate forward motion of the ultrasonic blade in the bone tissue.

Pursuant to another feature of the present invention, the operating of the ultrasonic waveform generator includes adjusting power output thereof to maintain a constant vibrational amplitude of the ultrasonic blade. Preferably, this is accomplished by adjusting voltage of the power output of the ultrasonic waveform generator while maintaining motional current and phase angle constant.

The controlling of the robotic subsystem preferably includes operating a digital processor of a control unit operatively connected to the servomechanisms.

In response to a drop in load or applied power as detected via a load sensor or pickup component, the ultrasonic waveform generator may be controlled to at least substantially reduce power output thereof automatically. The controlling of the robotic subsystem to reduce power output of the ultrasonic waveform generator may include operating a digital processor of a control unit operatively connected to the robotic subsystem.

BRIEF DESCRIPTION OF THE DRAWING

The sole FIGURE of the drawing is a block diagram of a surgical system in accordance with the present invention.

DETAILED DESCRIPTION

A surgical system for transecting osseous tissue in the close proximity of vitally important structures such as the spine has, as principal components or subsystems, an ultrasonic waveform generator 10, a control unit in the form of a digital processor 12, an ultrasonic instrument assembly 14 including an electromechanical transducer 16 and an ultrasonic blade 18, and a robotic system 20. Ultrasonic instrument assembly 14 is attached to a robotic arm 22 of system 20. Blade 18 is an integral or unitary part of a probe or tool 24 including a shank and a screw connector (neither shown separately) that couples the probe or tool to electromechanical transducer 16.

In order to ensure safe operation of the surgical system, there should be no sudden surges in the penetration speed of blade 18 at a breakthrough point, that is, at a point when blade 18 just penetrates through a distal side of a bone being cut. The surgical system is configured so that robotic arm 22 moves ultrasonic blade 18 at a constant forward feed speed through the bone during a cutting operation. Digital processor or control unit 12 is connected to a plurality of translational servomechanisms 26a, 26b, 26c and a plurality of rotation servomechanisms 28a, 28b, 28c that implement degrees of freedom necessary for instrument control. Digital processor or control unit 12 reduces forward motion of blade 18 through the bone tissue at a preselected surgical site and preferably halts the forward motion automatically upon a reduction in load per unit time or applied power, as monitored by a pickup or load sensor 30. Alternatively or additionally, power applied to transducer 16 by waveform generator 10 may be curtailed or interrupted.

Load sensor 30 may be part of a waveform generation subsystem 32, included in effect as part of waveform generator 10. The waveform generation control portion of digital processor 12, as well as the waveform generation subsystem 32 may take a form as described in U.S. Pat. Nos. 8,659,208 and 9,070,856, the disclosures of which are hereby incorporated by reference.

The constant feed speed of blade 18 is maintained by robotic arm 22 in response to the selective activation of servomechanisms 26a, 26b, 26c and 28a, 28b, 28c by digital processor or control unit 12. Load change pickup as detected via load sensor 30 is implemented in a feedback loop of the ultrasonic power application components (control unit 12, waveform generator 10, transducer 16), more precisely the variation of the drive voltage as a function of load. See U.S. Pat. Nos. 8,659,208 and 9,070,856. In order to maintain a constant motional amplitude, the ultrasonic controls maintain a constant motional current and phase angle while alternatively increasing and decreasing the ultrasonic voltage as a function of rising and falling load. At a breakthrough point, a voltage drop, associated with a decreased load, will be used as input to the servo controls (digital processor 12) for stopping or interrupting the operation of servomechanisms 26a, 26b, 26c and 28a, 28b, 28c. Additionally, the power output of the ultrasonic waveform generator 10 may be at least substantially reduced or interrupted.

Bone cutting blade 18 is formed at a distal end with a cutting edge 34 and may take the form shown in U.S. Pat. Nos. 6,379,371 and 6,443,969. Blade 18 is configured for transmitting ultrasonic vibrational energy, more specifically being dimensioned with probe 24 and transducer 16 to carry therewith an ultrasonic standing wave of desired frequency, exemplarily 22.5 KHz. As discussed above, control unit or processor 12 is operatively connected to robotic arm 22 and configured in part for controlling motion of robotic arm 22 so that the robotic arm moves the bone cutting blade 18 at a constant or uniform rate (speed) through bone tissue during a cutting operation. Electrical or ultrasonic waveform generator 10 is operatively connected to the ultrasonic electromechanical transducer 16 for energizing same to vibrate bone cutting blade 18 at the preselected (design) ultrasonic frequency. Processor 12 is operatively connected to the electrical waveform generator and configured therewith to monitor load on ultrasonic electromechanical transducer 16. Processor 12 is further configured to undertake, upon sensing a reduction in load or applied power (via input from load sensor 30), a control action of inducing the robotic arm 22 to halt motion of bone cutting blade 18 and/or at least substantially reducing waveform energy output of the ultrasonic electromechanical transducer 16.

An associated surgical method utilizing the illustrated surgical system typically includes mounting ultrasonic bone cutting blade 18 and ultrasonic electromechanical transducer 16 to robotic arm 22, and via servomechanisms 26a, 26b, 26c and 28a, 28b, 28c actuating the robotic arm to move the cutting blade at a constant or uniform rate through bone tissue during a surgical cutting operation. Electrical waveform generator 10 is operated to energize electromechanical transducer 16 to vibrate blade 18 at an ultrasonic frequency (e.g., 22.5 kHz) during the surgical cutting operation. The operating of waveform generator 10 includes adjusting power output thereof to maintain a constant vibrational amplitude of the ultrasonic bone cutting blade, as disclosed in U.S. Pat. Nos. 8,659,208 and 9,070,856. The method includes automatically monitoring load or power output of waveform generator 10 and, upon sensing a reduction in load or applied power, operating the servomechanisms 26a, 26b, 26c and 28a, 28b, to actuate robotic arm 22 to halt motion of blade 18 and optionally at least substantially reducing waveform energy output of waveform generator 10.

The operating of the electrical or ultrasonic waveform generator 10 includes adjusting power output thereof to maintain a constant vibrational amplitude of the ultrasonic blade 18. Preferably, this is accomplished by adjusting voltage of the power output of the ultrasonic waveform generator 10 while maintaining motional current and phase angle constant. See U.S. Pat. Nos. 8,659,208 and 9,070,856.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical system comprising:
    a bone cutting blade having a cutting edge, said bone cutting blade being configured for transmitting ultrasonic vibrational energy;
    an ultrasonic electromechanical transducer, said bone cutting blade being operatively connected to said ultrasonic electromechanical transducer;
    a robotic arm, said bone cutting blade being mounted to said robotic arm;
    a control processor operatively connected to said robotic arm, said processor configured in part for controlling motion of said robotic arm so that said robotic arm moves said bone cutting blade at a constant or uniform rate through bone tissue during a cutting operation; and
    an electrical waveform generator operatively connected to said ultrasonic electromechanical transducer for energizing same to energize said bone cutting blade with ultrasonic mechanical waveform energy,
    said processor being operatively connected to said electrical waveform generator and configured therewith to monitor load of said ultrasonic electromechanical transducer,
    said processor being further configured to undertake, upon sensing a reduction in load or applied power, a control action taken from the group consisting of inducing said robotic arm to halt motion of said bone cutting blade and at least substantially reducing waveform energy output of said electrical waveform generator.

2. A surgical system for transecting osseous tissue in close proximity to vitally important structures, comprising:
    an ultrasonic waveform generator;

a control unit operatively connected to said ultrasonic waveform generator;

an ultrasonic instrument assembly including an electromechanical transducer and an ultrasonic blade, said ultrasonic waveform generator being operatively connected to said transducer for energizing same; and a robotic subsystem including servomechanisms and a robotic arm movable by said servomechanisms, wherein:

a load sensor or pickup component is operatively connected said electromechanical transducer and included in said ultrasonic waveform generator, said load sensor or pickup component being operatively connected to said control unit;

said ultrasonic instrument assembly is attached to said robotic arm;

said control unit is operatively connected to said servomechanisms and configured to actuate said robotic arm so as to move said ultrasonic blade at a constant forward feed rate through bone tissue during a cutting operation;

said control unit being further configured to operate said servomechanisms, in response to a drop in load per unit time or applied power as detected by said load sensor or pickup component, to at least reduce forward motion of said ultrasonic blade through the bone tissue automatically.

3. A surgical system for transecting osseous tissue in close proximity to vitally important structures, comprising:

an ultrasonic waveform generator;

a control unit operatively connected to said ultrasonic waveform generator;

an ultrasonic instrument assembly including an electromechanical transducer and an ultrasonic blade, said ultrasonic waveform generator being operatively connected to said transducer for energizing same; and a robotic subsystem including servomechanisms and a robotic arm movable by said servomechanisms, wherein:

a load sensor or pickup component is operatively connected to said electromechanical transducer and included in said ultrasonic waveform generator, said load sensor or pickup component being operatively connected to said control unit;

said ultrasonic instrument assembly is attached to said robotic arm;

said control unit is operatively connected to said servomechanisms and configured to actuate said robotic arm so as to move said ultrasonic blade at a constant forward feed rate through bone tissue during a cutting operation;

said control unit being further configured to operate said servomechanisms, in response to a drop in load per unit time or applied power as detected by said load sensor or pickup component, to at least substantially reduce power output of said ultrasonic signal generator automatically.

4. A surgical method comprising:

providing an ultrasonic bone cutting blade operatively connected to an ultrasonic electromechanical transducer;

mounting said ultrasonic bone cutting blade and said ultrasonic electromechanical transducer to a robotic arm;

via a plurality of servomechanisms actuating said robotic arm to move said ultrasonic bone cutting blade at a constant or uniform rate through bone tissue during a surgical cutting operation;

operating an electrical waveform generator to energize said ultrasonic electromechanical transducer to vibrate said ultrasonic bone cutting blade at an ultrasonic frequency during said surgical cutting operation, the operating of said electrical waveform generator including adjusting power output thereof to maintain a constant vibrational amplitude of said ultrasonic bone cutting blade;

automatically monitoring load or power output of said electrical waveform generator; and upon sensing a reduction in load or applied power, undertaking a control action taken from the group consisting of operating said servomechanisms to actuate said robotic arm to halt motion of said ultrasonic bone cutting blade and at least substantially reducing waveform energy output of said electrical waveform generator.

5. The method defined in claim 4 wherein the adjusting of the power output of said electrical waveform generator to maintain a constant vibrational amplitude of said ultrasonic blade includes adjusting voltage of the power output while maintaining motional current and phase angle constant.

6. A surgical method for transecting osseous tissue in close proximity to vitally important structures, comprising:

operating an ultrasonic waveform generator to output an ultrasonic waveform signal of a preselected frequency;

feeding said ultrasonic waveform signal to an electromechanical transducer of an ultrasonic instrument assembly including an ultrasonic blade;

generating an ultrasonic standing wave in said ultrasonic instrument assembly including said ultrasonic blade;

controlling a robotic subsystem including servomechanisms and a robotic arm movable by said servomechanisms, to move said ultrasonic blade at a constant forward feed rate through bone tissue during a cutting operation, said ultrasonic instrument assembly being mounted to said robotic arm; and in response to a drop in load or applied power as detected via a load sensor or pickup component, controlling said robotic subsystem to terminate forward motion of said ultrasonic blade in the bone tissue.

7. The method defined in claim 6 wherein the operating of said ultrasonic waveform generator including adjusting power output thereof to maintain a constant vibrational amplitude of said ultrasonic blade.

8. The method defined in claim 7 wherein the adjusting of the power output of said electrical waveform generator to maintain a constant vibrational amplitude of said ultrasonic blade includes adjusting voltage of the power output while maintaining motional current and phase angle constant.

9. The method defined in claim 6 wherein the controlling of said robotic subsystem includes operating a digital processor of a control unit operatively connected to said servomechanisms.

10. A surgical method for transecting osseous tissue in close proximity to vitally important structures, comprising:

operating an ultrasonic waveform generator to output an ultrasonic waveform signal of a preselected frequency;

feeding said ultrasonic waveform signal to an electromechanical transducer of an ultrasonic instrument assembly including an ultrasonic blade;

generating an ultrasonic standing wave in said ultrasonic instrument assembly including said ultrasonic blade;

controlling a robotic subsystem including servomechanisms and a robotic arm movable by said servomechanisms, to move said ultrasonic blade at a constant forward feed rate through bone tissue during a cutting operation, said ultrasonic instrument assembly being mounted to said robotic arm; and in response to a drop in load or applied power as detected via a load sensor or pickup component, controlling said ultrasonic waveform generator to at least substantially reduce power output thereof automatically.

11. The method defined in claim 10 wherein the operating of said ultrasonic waveform generator including adjusting power output thereof to maintain a constant vibrational amplitude of said ultrasonic blade.

12. The method defined in claim 11 wherein the adjusting of the power output of said electrical waveform generator to maintain a constant vibrational amplitude of said ultrasonic blade includes adjusting voltage of the power output while maintaining motional current and phase angle constant.

13. The method defined in claim 10 wherein the controlling of said robotic subsystem includes operating a digital processor of a control unit operatively connected to said robotic subsystem, the controlling of said ultrasonic waveform generator including operating said digital processor.

* * * * *